US008853466B2

(12) United States Patent
Scates et al.

(10) Patent No.: US 8,853,466 B2
(45) Date of Patent: Oct. 7, 2014

(54) INTEGRATED PROCESS FOR PRODUCING ETHANOL FROM METHANOL

(75) Inventors: Mark O. Scates, Houston, TX (US); Ronald D. Shaver, Houston, TX (US); G. Paull Torrence, League City, TX (US); James H. Zink, League City, TX (US)

(73) Assignee: Celanese International Corporation, Dallas, TX (US)

( * ) Notice: Subject to any disclaimer, the term of this patent is extended or adjusted under 35 U.S.C. 154(b) by 564 days.

(21) Appl. No.: 13/213,765

(22) Filed: Aug. 19, 2011

(65) Prior Publication Data

US 2013/0046119 A1   Feb. 21, 2013

(51) Int. Cl.
C07C 29/149   (2006.01)
C07C 51/12    (2006.01)

(52) U.S. Cl.
CPC .............. C07C 29/149 (2013.01); C07C 51/12 (2013.01)
USPC ....................................................... 568/885

(58) Field of Classification Search
USPC ....................................................... 568/885
See application file for complete search history.

(56) References Cited

U.S. PATENT DOCUMENTS

| | | | |
|---|---|---|---|
| 2,607,807 A | 8/1952 | Ford | |
| 3,102,150 A | 8/1963 | Hunter et al. | |
| 3,478,112 A | 11/1969 | Karl et al. | |
| 4,126,539 A | 11/1978 | Derr, Jr. et al. | |
| 4,149,940 A | 4/1979 | Pinto | |
| 4,395,576 A | 7/1983 | Kwantes et al. | |
| 4,398,039 A | 8/1983 | Pesa et al. | |
| 4,421,939 A | 12/1983 | Kiff et al. | |
| 4,454,358 A | 6/1984 | Kummer et al. | |
| 4,497,967 A | 2/1985 | Wan | |
| 4,517,391 A | 5/1985 | Schuster et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,026,908 A | 6/1991 | Smith et al. | |
| 5,061,671 A | 10/1991 | Kitson et al. | |
| 5,070,016 A | 12/1991 | Hallberg | |
| 5,144,068 A | 9/1992 | Smith et al. | |
| 5,149,680 A | 9/1992 | Kitson et al. | |
| 5,414,161 A | 5/1995 | Uhm et al. | |
| RE35,377 E | 11/1996 | Steinberg et al. | |
| 5,599,976 A | 2/1997 | Scates et al. | |
| 6,143,930 A | 11/2000 | Singh et al. | |
| 6,232,352 B1 | 5/2001 | Vidalin et al. | |
| 6,326,515 B1 | 12/2001 | Clode et al. | |
| 6,458,996 B1 | 10/2002 | Muskett | |
| 6,472,555 B2 | 10/2002 | Choudary et al. | |
| 6,486,366 B1 | 11/2002 | Ostgard et al. | |
| 6,495,730 B1 | 12/2002 | Konishi et al. | |
| 6,509,180 B1 | 1/2003 | Verser et al. | |
| 6,627,770 B1 | 9/2003 | Cheung et al. | |
| 6,657,078 B2 | 12/2003 | Scates et al. | |
| 6,685,754 B2 | 2/2004 | Kindig et al. | |
| 6,906,228 B2 | 6/2005 | Fischer et al. | |
| 6,927,048 B2 | 8/2005 | Verser et al. | |
| 7,005,541 B2 | 2/2006 | Cheung et al. | |
| 7,084,312 B1 | 8/2006 | Huber et al. | |
| 7,115,772 B2 | 10/2006 | Picard et al. | |
| 7,208,624 B2 | 4/2007 | Scates et al. | |
| 7,507,562 B2 | 3/2009 | Verser et al. | |
| 7,553,397 B1 | 6/2009 | Colley et al. | |
| 7,608,744 B1 | 10/2009 | Johnston et al. | |
| 7,682,812 B2 | 3/2010 | Verser et al. | |
| 7,700,814 B2 | 4/2010 | Garton et al. | |
| 7,834,223 B2 | 11/2010 | Atkins et al. | |
| 7,842,844 B2 | 11/2010 | Atkins | |
| 7,863,489 B2 | 1/2011 | Johnston et al. | |
| 7,884,253 B2 | 2/2011 | Stites et al. | |
| 7,947,746 B2 | 5/2011 | Daniel et al. | |
| 8,071,821 B2 | 12/2011 | Johnston et al. | |
| 2006/0019360 A1 | 1/2006 | Verser et al. | |
| 2007/0238605 A1 | 10/2007 | Strehlau et al. | |
| 2007/0270511 A1 | 11/2007 | Melnichuk et al. | |
| 2009/0023192 A1 | 1/2009 | Verser et al. | |
| 2009/0069609 A1 | 3/2009 | Kharas et al. | |

(Continued)

FOREIGN PATENT DOCUMENTS

CN  101439256  5/2009
EP  0104197    4/1984

(Continued)

OTHER PUBLICATIONS

International Preliminary Report on Patentability for PCT/US2012/050737 mailed Mar. 6, 2014.
International Search Report and Written Opinion mailed on Nov. 30, 2012 in corresponding International Application No. PCT/US2012/050737.
U.S. Appl. No. 13/094,657, Not Yet Published, Lee, et al.
U.S. Appl. No. 13/094,588, Not Yet Published, Lee, et al.
U.S. Appl. No. 12/892,348, Not Yet Published, Torrence, et al.
Subramani et al., "A Review of Recent Literature to Search for an Efficient Catalytic Process for the Conversion of Syngas to Ethanol," Energy & Fuels, 2008, vol. 22, pp. 814-839.
Spivey et al., "Heterogeneous catalytic synthesis of ethanol from biomass-dervied syngas," Chemical Society Review, 2007, vol. 36, pp. 1514-1528.

(Continued)

Primary Examiner — Elvis O Price

(57) ABSTRACT

Processes and systems for forming ethanol from methanol. The process involves carbonylating the methanol to form acetic acid and hydrogenating the acetic acid to form ethanol. In a first aspect, at least some hydrogen for the hydrogenating step is derived from a tail gas stream formed in the carbonylation step. In a second aspect, at least some carbon monoxide for the carbonylation step is derived from a vapor stream in the hydrogenation system. In a third aspect, a syngas stream is separated to form a hydrogen stream and a carbon monoxide stream, and the hydrogen stream is methanated to remove residual carbon monoxide prior to being introduced into the hydrogenation system.

30 Claims, 5 Drawing Sheets

(56) References Cited

U.S. PATENT DOCUMENTS

| | | |
|---|---|---|
| 2009/0166172 A1 | 7/2009 | Casey |
| 2009/0221725 A1 | 9/2009 | Chorney et al. |
| 2009/0274480 A1 | 11/2009 | Zona |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0190547 A1 | 8/2011 | Jevtic et al. |
| 2011/0190548 A1 | 8/2011 | Jevtic et al. |
| 2011/0275862 A1 | 11/2011 | Johnston et al. |
| 2011/0275864 A1 | 11/2011 | Warner et al. |
| 2012/0010438 A1 | 1/2012 | Lee et al. |
| 2012/0010445 A1 | 1/2012 | Johnston et al. |

FOREIGN PATENT DOCUMENTS

| | | |
|---|---|---|
| EP | 0167300 | 1/1986 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| WO | WO 83/03409 | 10/1983 |
| WO | WO 02/092541 | 11/2002 |
| WO | WO 2005/102513 | 11/2005 |
| WO | WO 2007/003897 | 1/2007 |
| WO | WO 2009/009320 | 1/2009 |
| WO | WO 2009/063176 | 5/2009 |
| WO | WO 2009/105860 | 9/2009 |
| WO | WO 2010/055285 | 5/2010 |

OTHER PUBLICATIONS

Acala, et al., (2005). Experimental and DFT studies of the conversion of ethanol and acetic acid on PtSn-based catalysts, Journal of Physical Chemistry, 109(6), 2074-2085.

Baker, et al., "Membrane separation systems: recent developments and future directions", (1991) pp. 151-169.

Perry, et al., "Perry's Chemical Engineer's Handbook", 7th Ed., (1997), pp. 22-37 and 22-69.

A. Rehmat, et al., "Selective Methanation of Carbon Monoxide", Ind. Eng. Chem. Prod. Res. Develop., vol. 9, No. 4, pp. 512-515 (1970).

INTEGRATED PROCESS FOR PRODUCING ETHANOL FROM METHANOL

FIELD OF THE INVENTION

The present invention relates generally to processes for producing ethanol and, in particular, to producing ethanol from methanol via an acetic acid intermediate.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. In addition, integrated processes for making ethanol from various raw materials, such as biomass, via syngas, methanol and acetic acid intermediates, have also been proposed. See, e.g., U.S. Pat. Nos. 7,608,744; 7,863,489 and 7,884,253, the entireties of which are incorporated herein by reference. The need remains for improved processes for producing ethanol from commercially available materials, and in particular, for processes for forming ethanol having improved overall conversion and selectivity.

SUMMARY OF THE INVENTION

The present invention relates to integrated processes for forming ethanol from methanol via an acetic acid intermediate. In one embodiment, the present invention is directed to a process for forming ethanol, comprising the steps of: (a) carbonylating methanol in the presence of a carbonylation catalyst in a carbonylation reactor to form acetic acid and a tail gas stream, wherein the tail gas stream comprises carbon monoxide and hydrogen; (b) separating hydrogen, preferably with one or more membrane separation units, from the tail gas stream; and (c) hydrogenating the acetic acid with the separated hydrogen in the presence of a hydrogenation catalyst in a hydrogenation reactor to form a crude ethanol stream. Preferably, the process further comprises separating carbon monoxide from the tail gas stream and recycling the carbon monoxide to the carbonylation reactor.

In some aspects, the separating forms a hydrogen stream comprising hydrogen and residual carbon monoxide, and the process further comprises the step of reacting the residual carbon monoxide with hydrogen in the presence of a catalyst to form a methanated stream comprising hydrogen and methane. The methanated stream optionally comprises at least 85 vol. % hydrogen, e.g., at least 90 vol. % hydrogen or at least 95 vol. % hydrogen, and preferably less than 2 vol. % carbon monoxide, e.g., less than 1 vol. % carbon monoxide or less than 0.5 vol. % carbon monoxide. The tail gas preferably comprises at least 18 vol. % hydrogen, e.g., at least 25 vol. % hydrogen. Alternatively, the separating may form a hydrogen stream comprising hydrogen and residual carbon monoxide, and the process further comprises the step of reacting the residual carbon monoxide with methanol in the presence of a catalyst to form a stream comprising hydrogen and acetic acid.

Optionally, the process includes a step of preprocessing the tail gas prior to separating. For example, in one aspect, the tail gas at a temperature of 40-60° C., a pressure of 2.6-2.8 MPa, and a flow rate of 2000 $m^3$/hr-6000 $m^3$/hr is charged into a gas washing column, and contacts with top-down desalted water reversely in the column, and the acetic acid content in the acetic acid tail gas at the outlet of the gas washing column is equal to or less than 100 wppm. The tail gas from the gas washing column is charged into a mist eliminator to further remove droplets entrained therein, and the liquid level of the mist eliminator is controlled at 150-200 mm. The tail gas from the mist eliminator is then charged into a combined filter having a filter accuracy of 0.01 μm and in which the tail gas from the combined filter is optionally heated to 40-60° C. by a heater. The separating preferably comprises membrane separating, optionally with a Prism membrane separator at a pressure increasing rate equal to or less than 0.3 MPa/min. After membrane separation, the tail gas optionally is charged into a compressor at a flow rate of 1000 $m^3$/h-3000 $m^3$/h. The circulation of the desalted water of the gas washing column optionally is from 0.5 to 1.0 $m^3$/h. The acetic acid may be hydrogenated with the separated hydrogen and fresh hydrogen.

In another embodiment, the invention is to a reaction system for forming ethanol, comprising: (a) a carbonylation reactor for carbonylating methanol in the presence of a carbonylation catalyst to form acetic acid and a tail gas stream, wherein the tail gas stream comprises carbon monoxide and hydrogen; (b) a separation unit for separating hydrogen from the tail gas stream; and (c) a hydrogenation reactor for hydrogenating the acetic acid with the separated hydrogen in the presence of a hydrogenation catalyst to form a crude ethanol stream. The separation unit preferably comprises a membrane separation unit, e.g., a Prism membrane separator.

The system optionally further comprises a methanation unit in fluid communication with the separation unit for methanating a separated hydrogen stream to convert residual carbon monoxide contained therein to methane and water. The separation unit preferably also separates carbon monoxide from the tail gas stream, in which case the system preferably further comprises a conduit in fluid communication between the separation unit and the carbonylation reactor for recycling separated carbon monoxide from the separation unit to the carbonylation reactor. In one aspect, the system further comprises a gas washing column for contacting the tail gas stream with desalted water, a mist eliminator in fluid communication with the gas washing column for removing droplets entrained therein, and a combined filter in fluid communication with the mist eliminator for filtering the tail gas stream. Optionally, a fresh hydrogen source is provided for supplementing the hydrogenation reactor with fresh hydrogen. Alternatively, the system may further comprised a secondary carbonylation reactor in fluid communication with the separation unit, wherein the secondary carbonylation reactor reacts residual carbon monoxide contained in a separated hydrogen stream with methanol to form a secondary carbonylated stream comprising hydrogen and acetic acid.

In another embodiment, the invention is to a process for forming ethanol from methanol, comprising carbonylating the methanol to form acetic acid, and hydrogenating the acetic acid to form ethanol, wherein at least some hydrogen for the hydrogenating step is derived from a tail gas stream formed in the carbonylation step. The process preferably further comprises separating the tail gas to form a hydrogen stream and a carbon monoxide stream. Preferably at least a portion of the carbon monoxide stream is recycled to the carbonylation reactor. The process optionally further comprises methanating at least a portion of the hydrogen stream to remove residual carbon monoxide, in which case the process preferably also comprises a step of directing at least a portion of the methanated stream to the hydrogenation unit. Alternatively, the process may further comprise directing the hydrogen stream to a secondary carbonylation unit and carbonylating methanol therein with residual carbon monoxide contained in the hydrogen stream to form a secondary carbonylated stream comprising acetic acid and hydrogen and preferably less than 2 vol. % carbon monoxide. At least a portion of the secondary carbonylated stream may be directed to the hydrogenation unit.

BRIEF DESCRIPTION OF DRAWINGS

The invention is described in detail below with reference to the appended drawings, wherein like numerals designate similar parts.

DETAILED DESCRIPTION OF THE INVENTION

Introduction

In a first embodiment, the present invention relates to processes for producing ethanol from methanol via an acetic acid intermediate. The process involves the carbonylation of methanol in a carbonylation reactor to form acetic acid and hydrogenating the acetic acid in a hydrogenation reactor with hydrogen derived, at least in part, from a tail gas stream formed in the carbonylation process. Carbon monoxide (CO) may also be recovered from the tail gas and recycled to the carbonylation step.

In a second embodiment, the crude ethanol product is sent from the hydrogenation reactor to a separator unit, e.g., flash vessel, and carbon monoxide is recovered from separator unit and is recycled to the carbonylation reactor to form additional acetic acid. Hydrogen may also be recovered from the separator unit and recycled to the hydrogenation step and/or recycled to enhance stabilization of the carbonylation catalyst.

In a third embodiment, a syngas stream comprising carbon monoxide and hydrogen is separated into a hydrogen stream comprising hydrogen and residual carbon monoxide, and a carbon monoxide stream comprising carbon monoxide. At least a portion of the hydrogen stream is methanated to convert at least a portion of the residual carbon monoxide to methane and water and forming a methanated hydrogen stream. An alkanoic acid, preferably acetic acid, is hydrogenated with hydrogen from the methanated hydrogen stream in the presence of a catalyst under conditions effective to form the alcohol, preferably ethanol. Optionally, all or a portion of the carbon monoxide stream may be directed to a carbonylation unit for the synthesis of the alkanoic acid, preferably acetic acid.

Figure 1:
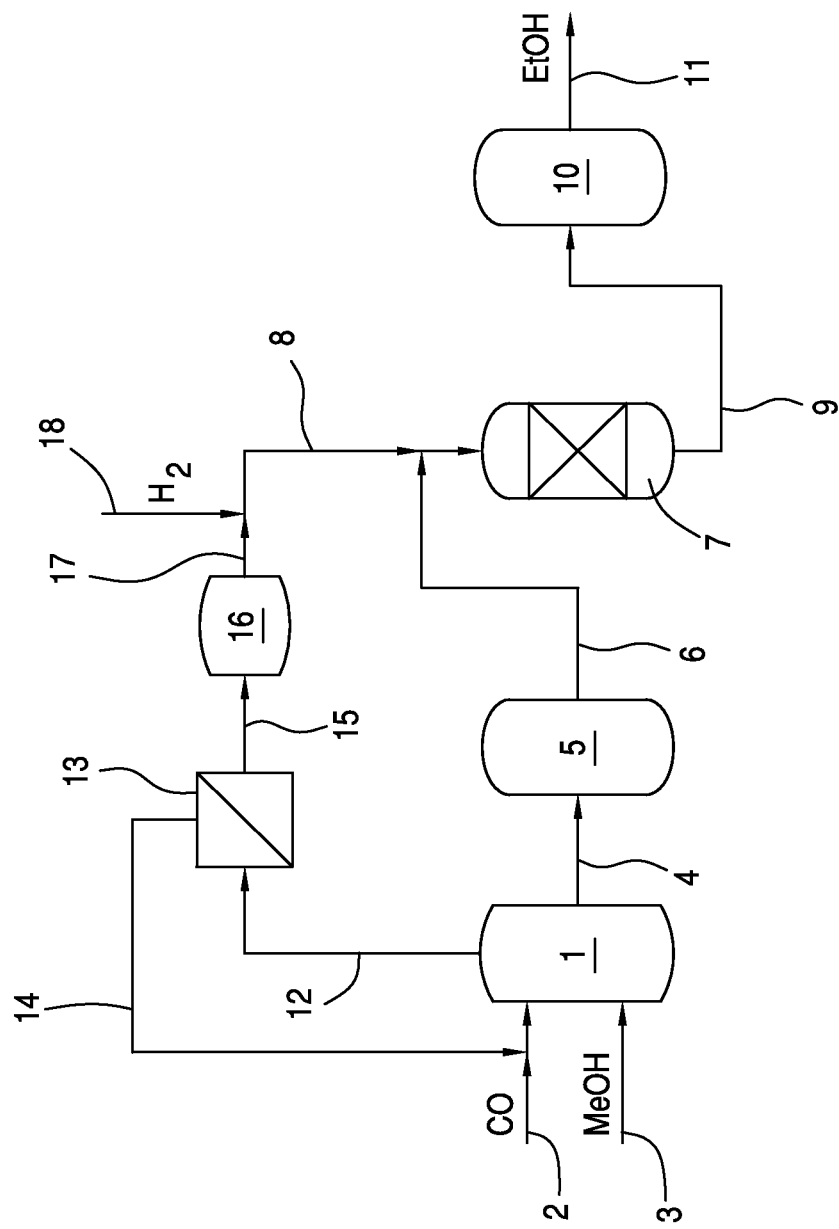
FIG. 1 is a schematic flow diagram of a first embodiment of the invention.
Figure 2:
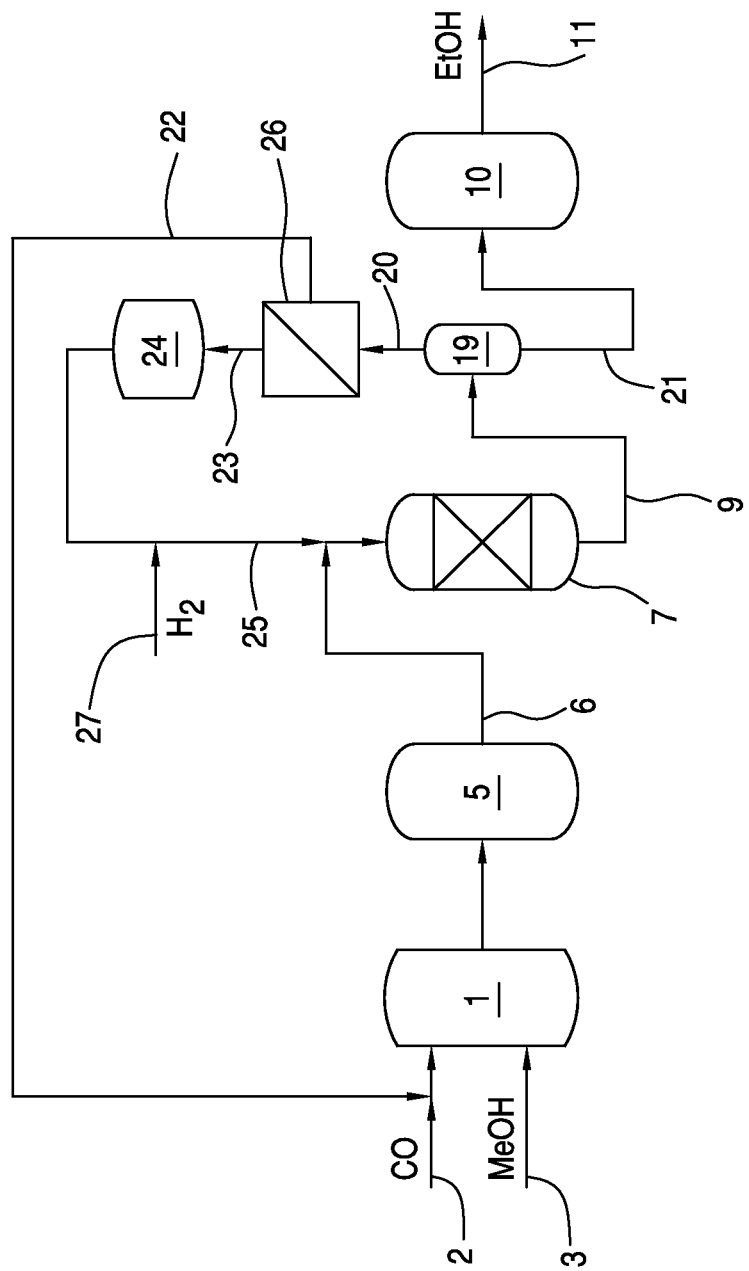
FIG. 2 is a schematic flow diagram of a second embodiment of the invention.
Figure 3:
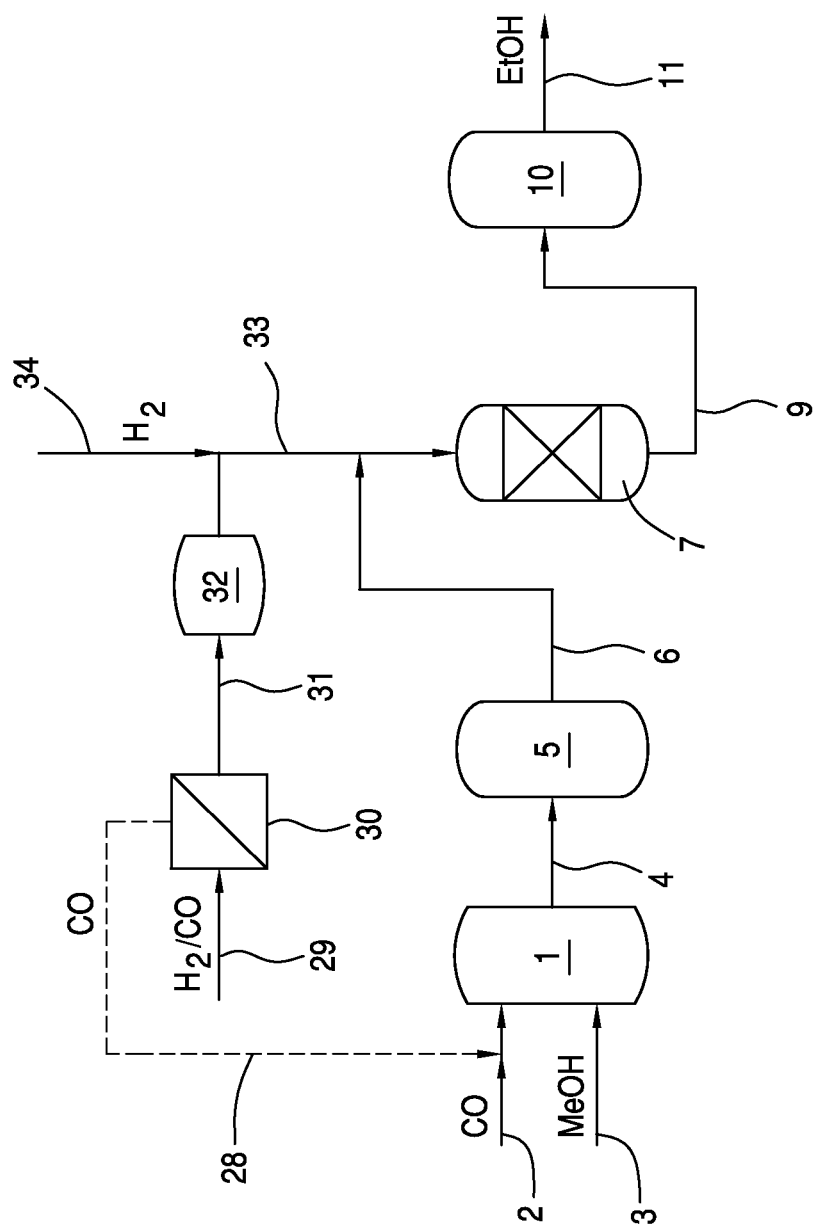
FIG. 3 is a schematic flow diagram of a third embodiment of the invention.

FIGS. 1-3 illustrate process flow schemes according to the three embodiments of the invention. As shown, carbonylation reactor 1 receives a carbon monoxide stream 2 and a methanol stream 3 and forms a crude acetic acid stream 4. Crude acetic acid stream 4 is separated in a separation zone 5 to form a purified acetic acid stream 6, which is sent to a hydrogenation reactor 7. In hydrogenation reactor 7, acetic acid from purified acetic acid stream 6 is hydrogenated with hydrogen from hydrogen stream 8 to form a crude ethanol product 9, which is sent to a separation zone 10 to form a final ethanol product 11.

Figure 4:
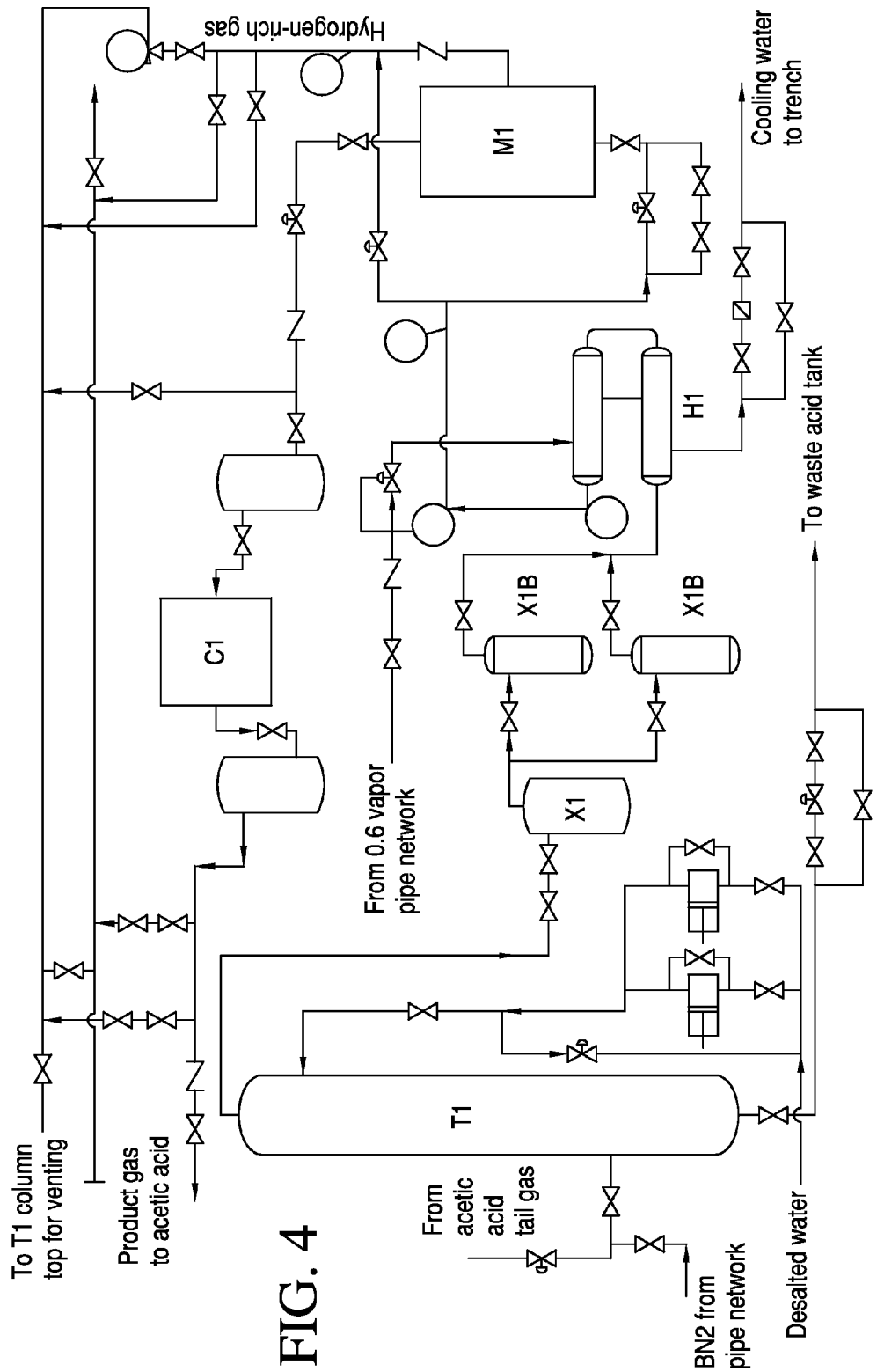
FIG. 4 is a flow chart of acetic acid high-pressure tail gas process, which includes a gas pre-treatment system before feeding to a membrane separator and which may be adopted in the first embodiment of the invention.
Figure 5:
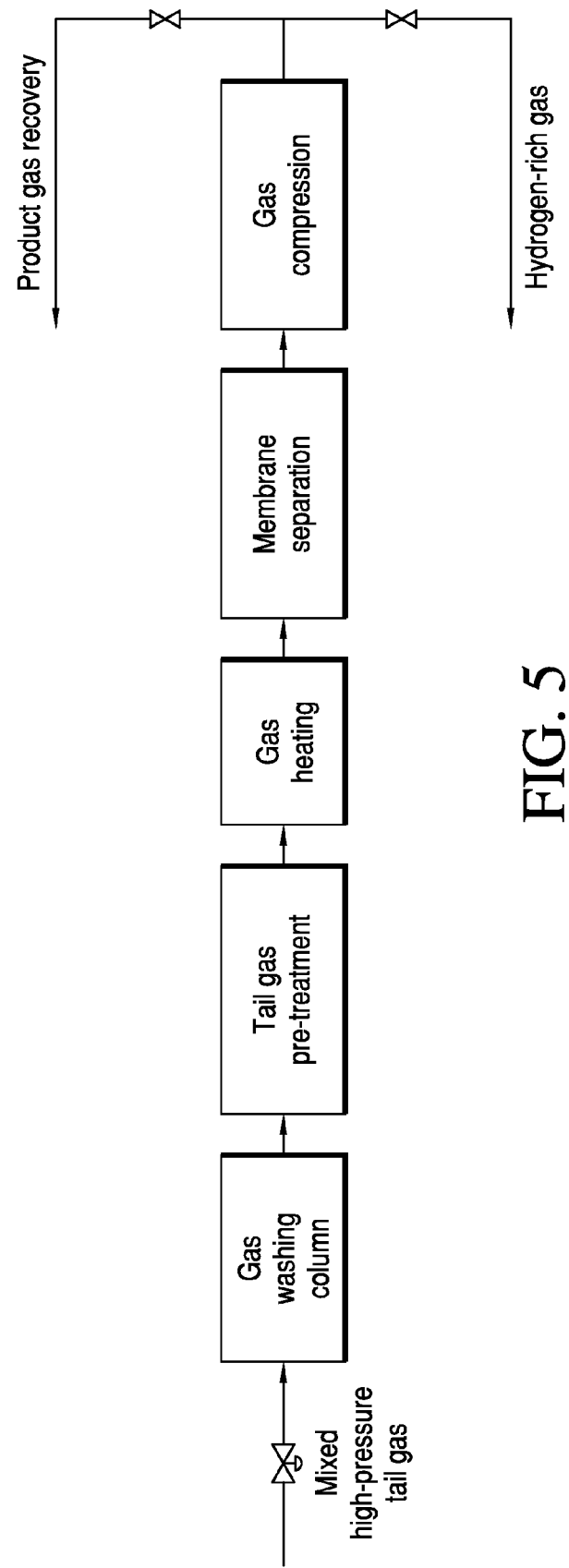
FIG. 5 is a schematic flow chart of acetic acid high-pressure tail gas recovery for the first embodiment of the invention.

According to a first embodiment of the invention, shown in FIG. 1, tail gas 12 comprising carbon monoxide and hydrogen is sent to a membrane separator 13, optionally after pretreating as described below with reference to FIGS. 4 and 5. Membrane separator 13 preferably separates the tail gas into a carbon monoxide product stream 14 and a hydrogen stream 15. As discussed herein, membrane separator 13 may comprise a single membrane separation unit or multiple membrane separation units to provide a hydrogen stream 15 having the desired hydrogen concentration. Suitable membranes include shell and tube membrane modules having one or more porous material elements therein. Non-porous material elements may also be included. The material elements may include polymeric element such as polyvinyl alcohol, cellulose esters, and perfluoropolymers. Membranes that may be employed in embodiments of the present invention include those described in Baker, et al., "Membrane separation systems: recent developments and future directions," (1991) pages 151-169, Perry et al., "Perry's Chemical Engineer's Handbook," 7th ed. (1997), pages 22-37 to 22-69, the entireties of which are incorporated herein by reference. Hydrogen permeable membranes are preferred.

The carbon monoxide product stream 14 is preferably recycled to the carbonylation reactor 1, and hydrogen stream 15 preferably is sent to methanation unit 16. Residual carbon monoxide contained in the hydrogen stream 15 is converted to methane in methanation unit 16 to form a methanated hydrogen stream 17, which is sent to hydrogenation reactor 7. Fresh hydrogen via stream 18 optionally is combined with methanated hydrogen stream 17 to form hydrogen stream 8, which is sent to the hydrogenation reactor 7.

In another embodiment, not shown, methanation unit 16 is replaced with a carbonylation reactor, optionally a secondary carbonylation reactor, which operates to reduce the carbon monoxide concentration by reacting the carbon monoxide with methanol, which is optionally added to stream 15 or to the carbonylation reactor, to form acetic acid. The acetic acid may then be added to the hydrogenation reactor 7 to form additional ethanol. See, e.g., U.S. patent application Ser. No. 12/892,348, the entirety of which is incorporated herein by reference, which describes the use of a secondary carbonylation reactor.

In the second embodiment of the invention, shown in FIG. 2, crude ethanol product 9 is sent to a separator 19, e.g., a flash vessel or absorber (optionally a methanol absorber to remove residual acetic acid), which forms flash stream 20 and a liquid crude products stream 21. Flash stream 20 comprises hydrogen and a minor amount of carbon monoxide, and is directed to a membrane separator 26, optionally after pretreating as described below. Membrane separator 26 preferably separates carbon monoxide in carbon monoxide product stream 22 from a hydrogen stream 23. The carbon monoxide product stream 22 is preferably recycled to the carbonylation reactor 1, and hydrogen stream 23 preferably is sent to methanation unit 24. Residual carbon monoxide contained in the hydrogen stream 23 is converted to methane in methanation unit 24 to form a methanated hydrogen stream 25, which is sent to hydrogenation reactor 7. Fresh hydrogen via stream 27 optionally is combined with methanated hydrogen stream 25 and sent to the hydrogenation reactor 7.

In another, not shown, methanation unit 24 is replaced with a carbonylation reactor, which operates to reduce the carbon monoxide concentration by reacting the carbon monoxide with methanol, which is optionally added to stream 23 or to the carbonylation reactor, to form acetic acid. The acetic acid may then be added to the hydrogenation reactor 7 to form additional ethanol.

In the third embodiment of the invention, a syngas stream 29 comprising hydrogen and carbon monoxide is sent to a membrane separator 30, optionally after pretreating as described below with reference to FIGS. 4 and 5. Membrane separator 30 preferably separates carbon monoxide in carbon monoxide product stream 28 from a hydrogen stream 31. The carbon monoxide product stream 28 is optionally directed to carbonylation reactor 1 to serve as the carbon monoxide source for the carbonylation of methanol (or other alcohol), and hydrogen stream 31 preferably is sent to methanation unit 32. Residual carbon monoxide contained in the hydrogen stream 31 is converted to methane in methanation unit 32 to form a methanated hydrogen stream 33, which is sent to hydrogenation reactor 7. Fresh hydrogen via stream 34 optionally is combined with methanated hydrogen stream 33 to form a combined hydrogen stream that is sent to the hydrogenation reactor 7.

In another embodiment, the various embodiments may be combined together in various combinations. For example, the first embodiment of the invention may be combined with the second embodiment of the invention, the second embodiment may be combined with the third embodiment, the first embodiment may be combined with the third embodiment, or all three embodiments may be combined. Although the subject disclosure is directed primarily to the use of membrane separation units for separating hydrogen/carbon monoxide streams into a hydrogen stream and a carbon monoxide stream, other separation techniques may also be used, e.g., liquefaction or by separation columns, e.g., cryogenic separation columns, pressure swing adsorption (PSA) units, amine scrubbing, and the like.

Acetic Acid Synthesis

The present invention relates to processes for hydrogenating acetic acid to form ethanol. The acetic acid, in turn, is formed from the carbonylation of methanol. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with carbon monoxide generation for a new acetic acid plant are significantly reduced or largely eliminated. All or part of the syngas is diverted from the methanol synthesis loop and supplied to a separator unit to recover carbon monoxide, which is then used to produce acetic acid. In a similar manner, hydrogen for the hydrogenation step may be supplied from syngas, although in the first embodiment at least a portion of the hydrogen in the hydrogenation step preferably is derived from the tail gas formed in the carbonylation process, and in the second embodiment at least a portion of the hydrogen in the hydrogenation step is recycled from a separator vessel downstream of the hydrogenation reactor.

In some embodiments, some or all of the raw materials for the acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas, although in the first embodiment at least a portion of the hydrogen preferably is derived from the tail gas formed in the carbonylation process. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

In the first embodiment, a process and unit for carbon monoxide and hydrogen recovery from high-pressure tail gas of carbonylation to acetic acid by membrane method are provided, in which the tail gas is subjected to pre-treatment, membrane separation, and gas compression. Aspects of this process may also be adapted to the second embodiment of the invention. The tail gas passing through a gas washing column, a mist eliminator, and a combined filter is heated by a heater, and then charged into a membrane separator, e.g., a Prism membrane separator; the recovered carbon monoxide product gas after membrane separation is charged into a compressor, the carbon monoxide is recovered for reuse, and (for the first embodiment) the hydrogen-rich gas (hydrogen stream) is charged to a hydrogenation reactor, optionally after a methanation step, for the production of ethanol, as discussed below. By using two sets of membrane systems, e.g., Prism membrane separator systems, the gas amounts of the raw gas fed into the membrane, the product gas, and the hydrogen-rich gas are controlled to reach a $N_2$ material balance, to ensure carbon monoxide and hydrogen recovery rate, so as to achieve long-term stable running of the membrane separation unit. The content of carbon monoxide in the final product gas is preferably equal to or greater than 91 vol. %. Processes for separating carbon monoxide from an acetic acid tail gas stream are described in CN 101439256 A, the entirety of which is incorporated herein by reference.

The present invention provides a process for carbon monoxide and hydrogen recovery by one or more membranes from high-pressure tail gas of a methanol carbonylation reactor, in which carbon monoxide and hydrogen in the tail gas after pre-treatment are recovered by a membrane separation method, and the carbon monoxide content in the product gas is equal to or greater than 91% (molar percentage). The resulting hydrogen stream (before optional methanation) preferably comprises at least 18 vol. % hydrogen, e.g., at least 20 vol. % hydrogen, at least 25 vol. % hydrogen, at least 50 vol. % hydrogen, at least 75 vol. % hydrogen or at least 85 vol. % hydrogen. In terms of ranges, the resulting hydrogen stream optionally comprises from 18 to 99 vol. % hydrogen, from 25 to 97 vol. % hydrogen, or from 75 to 95 vol. % hydrogen. The hydrogen content of the hydrogen enriched stream may be advantageously increased to a desired level by using multiple separation stages, if desired.

In one embodiment, the technical solution of the present invention is a process for carbon monoxide and hydrogen recovery from high-pressure tail gas of carbonylation to acetic acid by a membrane method, in which the tail gas is subjected to three steps: pre-treatment, membrane separation, and gas compression. The resulting hydrogen stream is directed to a hydrogenation reactor for converting acetic acid to ethanol, as described below.

In one optional pretreatment process, a high-pressure mixed acetic acid tail gas at a temperature of 40-60° C., a pressure of 2.6-2.8 MPa, and a flow rate of 2000 $m^3$/h-6000 $m^3$/h is charged into a gas washing column, and contacts top-down desalted water reversely in the column. The acetic acid content in the acetic acid tail gas at the outlet of the gas washing column may be equal to or less than 100 wppm, and the circulation of the desalted water of the gas washing column may be from 0.5-1.0 $m^3$/h. The tail gas from the gas washing column may be charged into a mist eliminator to further remove droplets entrained therein, and the liquid level of the mist eliminator may be controlled at 150-200 mm. The tail gas from the mist eliminator may be charged into a combined filter with a filter accuracy of about 0.01 μm. The tail gas from the combined filter may be heated to 40-60° C. with a heater.

In an optional membrane separation step, the tail gas after pre-treatment is charged into a membrane separator, e.g., a Prism membrane separator, at a pressure increasing rate equal to or less than 0.3 MPa/min.

In an optional gas compression step, the tail gas, specifically the separated carbon monoxide product gas derived therefrom, after membrane separation is charged into a compressor at a flow rate of 1000 $m^3$/h-3000 $m^3$/h. The carbon monoxide product gas is preferably recovered for reuse, and the hydrogen-rich gas (hydrogen stream) is preferably charged to a hydrogenation unit with acetic acid to form ethanol.

A unit used in the process for carbon monoxide and hydrogen recovery from high-pressure tail gas of carbonylation to acetic acid by membrane method mainly includes a gas washing column, a mist eliminator, a combined filter, a heater, a membrane separator, and a compressor. The gas washing column is connected to the mist eliminator through a conduit, the mist eliminator is connected to the combined filter through a conduit, the combined filter is connected to the heater through a conduit, the heater is connected to the separator through a conduit, and the separator is connected to the compressor through a conduit. The membrane separator optionally comprises a total of 20 to 50 membrane components, preferably about 32 membrane components in one, two or more sets, although in some embodiments, more membrane components and stages may be desired to form a hydrogen stream of sufficiently high hydrogen content for being directed to a methanation unit and subsequent hydrogenation reactor. The membranes may also comprise polyimide hollow fiber membranes.

Beneficial Effects

1. The components that may damage the membrane, such as methyl iodide, acetic acid, water, in the high-pressure tail gas of carbonylation to acetic acid preferably are substantially removed through the gas washing column. In a preferred embodiment, the high-pressure acetic acid tail gas at a stable flow rate is charged into an adsorption column having a tray structure and equipped with a pre-treatment system, and contacts with top-down desalted water reversely in the column. In this manner, harmful components in the tail gas, such as acetic acid and water, may be removed by controlling the circulation of water supply such that the acetic acid content in the tail gas is equal to or less than 100 ppm, e.g., equal to or less than 50 ppm.

2. Droplets entrained in the tail gas may be removed by the mist eliminator, to reduce or eliminate the influence of such droplets on the effect of membrane separation and damage on the membrane components.

3. Impurity particulates in the tail gas preferably are removed by the combined filter to reduce and minimize the potential for damage to the membrane components.

4. The high-pressure mixed acetic acid tail gas is preferably at a pressure of 2.6-2.8 MPa and a flow rate of 2000 $m^3$/h-6000 $m^3$/h. The flow rate of the recovered carbon monoxide product gas and/or recovered hydrogen stream preferably is controlled at 1000 $m^3$/h-3000 $m^3$/h to avoid the influence of $N_2$ accumulation on the long-term stable running of the membrane system.

5. In this process, by using a vapor heater, the temperature of the mixed gas is preferably increased so as to avoid the water dew point to enter into the membrane system for separation. After being charged into the shell of the membrane separator, the mixed tail gas flows along outside of the fiber, and hydrogen gas selectively and preferentially permeates through the wall of the fiber membrane and is enriched at a low-pressure side in the pipe. The resulting hydrogen stream is then introduced out of the membrane separation system as a feed to the acetic acid hydrogenation step, described below. In a preferred embodiment, the hydrogen stream is directed to a methanation unit for reducing the amount of any residual carbon monoxide that is contained therein. Meanwhile, carbon monoxide and nitrogen with low permeation rate are reserved at a non-permeated gas side and have a pressure similar to that of the raw gas and are introduced out of the system as carbon monoxide product gas for compression and optionally recycle to the carbonylation step. According to the present invention, the recovery rate is controlled by adjusting the flow rates of the raw gas, the hydrogen-rich gas stream and the carbon monoxide product gas, and the pressure of the carbon monoxide product gas is increased through a gas compressor to be balanced with the system pressure and integrated into the system.

6. The process for recovery and reuse of acetic acid high-pressure tail gas with membranes according to the present invention has the additional advantages that there is no phase transition, the energy consumption is low and the unit scale can be adjusted according to the requirement of the gas amount being treated, compared with pressure swing adsorption separation technique. Furthermore, the process has the advantage of being a simple unit, with convenient operation, and high running reliability.

A non-limiting exemplary separation system according to one embodiment of the invention is provided below with reference to FIGS. 4 and 5.

1. Gas washing column T1

The flow rate of the acetic acid mixed high-pressure tail gas is preferably 2000 $m^3$/h-6000 $m^3$/h, the working pressure of the gas washing column is preferably 2.6-2.8 MPa, the temperature is preferably 40-60° C. The column has 22 stainless steel floating valve trays therein, and the mass content of acetic acid in the absorption solution after the acetic acid high-pressure tail gas passes through the gas washing column is preferably about 30%.

Desalted water is pumped to the top of the gas washing column by a circulation pump of the column and contacts the acetic acid high-pressure tail gas reversely. The circulation of the desalted water is preferably 0.5-1.0 $m^3$/h and may be adjusted according to the acetic acid content in the tail gas, such that the acetic acid content in the acetic acid high-pressure tail gas at the outlet of the gas washing column is equal to or less than 100 wppm, e.g., equal to or less than 50 wppm.

The flow rate of the water supply of the gas washing column is controlled to be stable, the liquid level at the bottom is stabilized, and the waste acid solution is recovered for reuse.

2. Mist eliminator X1: The mist eliminator can remove droplets entrained in the acetic acid high-pressure tail gas effectively. The liquid level of the mist eliminator is preferably controlled at 150-200 mm, and the liquid is discharged regularly. The separator has an interlock protection device for liquid level to prevent severe gas-liquid entrainment from causing adverse effect on the membrane life.

3. Combined filter X1B: The combined filter can remove particulates entrained in the acetic acid high-pressure tail gas to prevent them from blocking the membranes and influencing the membrane separation effect. The filter precision is preferably about 0.01 μm, and the stability of the filter is ensured by monitoring the pressure difference.

4. Heater E1: After the above processing, the acetic acid high-pressure tail gas is not a saturated gas, and water will impact the use of the membrane. At 0.6 MPa low-pressure vapor, the tail gas is preferably heated to 40-60° C. such that the tail gas avoids the dew point. The control, indication, alarm, and interlock of temperature may be realized by using a vapor flow rate regulating valve and a temperature transducer so as to maintain the gas temperature at constant value. The cooling water of the entire unit may be discharged to waste water treatment.

5. Prism membrane separator M1

The separation membrane used in the unit may comprise any suitable membranes for separating carbon monoxide from hydrogen. In one aspect, the membranes comprise hollow fiber membranes, e.g., Prism membranes, and the membrane material comprises polyimide. The separator includes a total of at least 32 membrane components in two sets. Additional membranes and stages may be employed to obtain the desired hydrogen/carbon monoxide separation.

The pressure increasing rate of the membrane separator preferably is equal to or less than 0.3 MPa/min. When the pressure of the membrane separator is increased to be balanced with the pressure of the previous system, it is required to open the raw gas inlet valve, product carbon monoxide outlet valve, and hydrogen-rich gas outlet valve of each set of membrane separator to be used.

The pressure, flow rate, and carbon monoxide content of the product gas are controlled and adjusted through a regulating valve, to ensure the pressure at the inlet of the tail gas compressor to be stable.

As discussed, each of the different embodiments of the invention may employ one or more membrane separation units to separate a hydrogen stream and a carbon monoxide stream from a process stream. In the third embodiment, the one or more separation units separate a hydrogen stream and a carbon monoxide stream from a syngas stream. The syngas stream before separation optionally has a hydrogen to carbon monoxide molar ratio less than 3:1, less than 2:1, less than 1:1 or less than 0.5:1. The processes of the invention, however, provide the ability to form a separated hydrogen stream (before or after optional methanation) having a ratio preferably greater than 2:1, greater than 5:1, or greater than 10:1, and optionally a carbon monoxide stream having a ratio less than 1:1, less than 0.5:1, less than 0.25:1 or less than 0.1:1.

6. Compressor C1

The flow rate of the product gas is preferably 1000 $m^3$/h-3000 $m^3$/h, and the pressure of the membrane carbon monoxide product gas is increased by the tail gas compressor from 2.1-2.3 MPa to the use pressure of the next step, and it is combined into the acetic acid system for recovery and reuse.

Control of the recovery amount and recovery rate of the acetic acid tail gas.

Recovery amount: The membrane recovery unit can realize the recovery and reuse of carbon monoxide, but nitrogen gas cannot be separated effectively, thus causing accumulation of nitrogen gas in the system. According to the present invention, continuous recovery of the tail gas is realized by adjusting the torch venting amount and the recovery amount of the tail gas. Adjustment and balance of the recovery amount of the high-pressure tail gas of the unit are realized through the calculation of the nitrogen material balance in the acetic acid carbon monoxide pipe of the current unit, thus keeping the recovery amount of nitrogen and the venting amount of the hydrogen-rich gas to be consistent.

Recovery rate: The Prism membrane system can ensure long-term carbon monoxide recovery from acetic acid high-pressure tail gas at the largest amount, and the carbon monoxide content to be equal to or greater than 91%. By adjusting gas amount fed into the membrane and the product gas amount, the acetic acid high-pressure tail gas is recovered and reused at the maximum extent, while ensuring the carbon monoxide proportion in the acetic acid pipe.

With the pre-treatment system consisting of the gas washing column, the mist eliminator, and the combined filter, "harmful" components in the tail gas are removed, to prevent the influence on the stable running of the membrane. In practice, multiple sets of membranes are adopted to realize effective separation of the tail gas, and the processed gas amount, the carbon monoxide product gas composition, and the hydrogen stream meet the working requirements. The material balance may be calculated and the gas amount of the product gas fed into acetic acid may be adjusted over time to prevent $N_2$ accumulation.

Methanation of Hydrogen Stream

As indicated above, the hydrogen stream from the membrane separator may comprise substantial amounts of carbon monoxide in addition to hydrogen. Depending on the catalyst employed in the subsequent hydrogenation process, carbon monoxide may not be well tolerated in the hydrogenation step. As a result, in the first embodiment of the invention, it may be desired to reduce the amount of carbon monoxide contained in the hydrogen stream prior to sending the hydrogen stream to the hydrogenation process. One technique for reducing the carbon monoxide content of the hydrogen stream includes methanation, and in a preferred embodiment, the invention includes a step of methanating the hydrogen stream prior to directing it to the hydrogenation process.

In the second embodiment of the invention, a crude ethanol product is directed from the hydrogenation reactor to a separator unit, e.g., a flash vessel, which forms a vapor stream and a liquid ethanol product stream. The vapor stream is separated into a carbon monoxide stream and a hydrogen stream, which may comprise residual carbon monoxide. Since carbon monoxide may not be well tolerated in the hydrogenation process, the carbon monoxide content of the hydrogen stream also may be further reduced through methanation.

In the third embodiment of the invention, a syngas stream comprising hydrogen and carbon monoxide is separated in a separation unit, preferably comprising one or more membrane separation units, to form a carbon monoxide stream and a hydrogen stream, which may comprise residual carbon monoxide. As with the above embodiments, since carbon monoxide may not be well tolerated in the hydrogenation process, the carbon monoxide content of the hydrogen stream also may be further reduced through methanation.

Processes for methanating carbon monoxide-containing streams are described, for example, in A. Rehmat et al., "Selective Methanation of Carbon Monoxide," *Ind. Eng. Chem. Prod. Res. Develop.*, Vol. 9, No. 4, pp. 512-515 (1970), the entirety of which is incorporated herein by reference.

During the methanation process, each mole of carbon monoxide reacts with three moles of hydrogen to form methane, which is unreactive under typical hydrogenation conditions, and water. Thus, hydrogen should be present in the hydrogen stream in at least a 3:1 molar excess relative to the amount of carbon monoxide contained in the hydrogen stream and should have sufficient excess hydrogen in order to have residual hydrogen remaining in the methanated hydrogen stream to serve as a hydrogen source for the hydrogenation reaction. In some exemplary embodiments, the molar ratio of hydrogen to carbon monoxide in the hydrogen stream before methanation is at least 3.5:1, at least 4:1 or at least 5:1.

The methanation step is preferably conducted in a methanation reactor under methanation conditions. The methanation conditions may vary widely, but in one embodiment, the methanation step is conducted at a temperature from 125° C. to 300° C., which provides a negligible amount of reverse shift reaction while providing vigorous carbon monoxide methanation. Because the methanation reaction is exothermic, the temperature will increase over the course of the reaction. Preferably, the reaction is maintained at a methanation temperature below 300° C., preferably below 250° C., or a temperature between 200° C. and 250° C. At greater temperatures, more carbon monoxide may be undesirably produced.

The methanation step preferably is conducted in the presence of a methanation catalyst. Exemplary methanation catalysts may include one or more metals selected from the group consisting of ruthenium, nickel and aluminum. For example, the catalyst may comprise ruthenium (e.g., ruthenium on α-alumina), IGT Raney nickel (e.g., 30-35% nickel, 5% aluminum, and 60% $Al_2O_3$-$3H_2O$), Harshaw nickel (e.g., 58% Ni on kieselguhr), CCI nickel (e.g., 47% nickel oxide on alumina), or Girdler G-65 (nickel on α-alumina).

Although the composition of the hydrogen stream after methanation may vary depending on the composition of the initial hydrogen stream and the methanation conditions, the methanated hydrogen stream for the first embodiment preferably comprises at least 85 vol. % hydrogen, e.g., at least 90 vol. % hydrogen or at least 95 vol. % hydrogen. The methanated hydrogen stream for the first embodiment preferably comprises less than 2 vol. % carbon monoxide, e.g., less than 1 vol. % carbon monoxide or less than 0.5 vol. % carbon monoxide. The methanated hydrogen stream for the second embodiment will generally comprise a greater amount of hydrogen, and preferably comprises at least 90 vol. % hydrogen, e.g., at least 95 vol. % hydrogen or at least 99 vol. % hydrogen. The methanated hydrogen stream for the second embodiment preferably comprises less than 2 vol. % carbon monoxide, e.g., less than 1 vol. % carbon monoxide or less than 0.5 vol. % carbon monoxide.

Hydrogenation of Acetic Acid

As discussed above, in the first embodiment, hydrogen derived from the carbonylation process tail gas preferably is used in the hydrogenation of acetic acid to form ethanol. In the second embodiment, hydrogen derived from the separator vapor stream preferably is recycled to the hydrogenation reactor. The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIB, VIIB, VIII transition metals, a lanthanide metal, an actinide metal or a metal selected from any of Groups IIIA, IVA, VA, and VIA. In one embodiment, the catalyst comprises platinum and/or palladium. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 $m^2$/g; median pore diameter of about 12 nm; average pore volume of about 1.0 $cm^3$/g as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Several different separation schemes may be employed in purifying the crude ethanol product of the present invention. See, for example, US Published Application US20110190547, the entirety of which is incorporated herein by reference, and U.S. patent application Ser. Nos. 12/852,305, 13/094,691, 13/094,537, 13/094,588, and 13/094,657, the entireties of which are incorporated herein by reference. As discussed above, the separation scheme preferably includes a separator unit, e.g., a flash vessel, for separating a vapor stream from a liquid crude ethanol product. The vapor stream preferably comprises hydrogen and carbon monoxide, which according to the second embodiment of the invention may be separated in one or more membrane separators to form a hydrogen stream and a carbon monoxide stream. The carbon monoxide stream preferably is recycled to the carbonylation reactor and the hydrogen stream preferably is recycled to the hydrogenation reactor, optionally after methanation thereof to remove residual carbon monoxide.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for forming ethanol, comprising the steps of:
   (a) carbonylating methanol in the presence of a carbonylation catalyst in a carbonylation reactor to form acetic acid and a tail gas stream, wherein the tail gas stream comprises carbon monoxide and hydrogen;
   (b) separating hydrogen from the tail gas stream; and
   (c) hydrogenating the acetic acid with the separated hydrogen in the presence of a hydrogenation catalyst in a hydrogenation reactor to form a crude ethanol stream.

2. The process of claim 1, further comprising separating carbon monoxide from the tail gas stream and recycling the carbon monoxide to the carbonylation reactor.

3. The process of claim 1, wherein the separating comprises membrane separating.

4. The process of claim 1, wherein the separating forms a hydrogen stream comprising hydrogen and residual carbon monoxide, the process further comprising the step of reacting the residual carbon monoxide with hydrogen in the presence of a catalyst to form a methanated stream comprising hydrogen and methane.

5. The process of claim 4, wherein the methanated stream comprises at least 85 vol. % hydrogen.

6. The process of claim 4, wherein the methanated stream comprises less than 2 vol. % carbon monoxide.

7. The process of claim 1, wherein the separating forms a hydrogen stream comprising hydrogen and residual carbon monoxide, the process further comprising the step of reacting the residual carbon monoxide with methanol in the presence of a catalyst to form a stream comprising hydrogen and acetic acid.

8. The process of claim 1, wherein the tail gas stream comprises at least 18 vol. % hydrogen.

9. The process of claim 1, wherein the tail gas stream comprises at least 25 vol. % hydrogen.

10. The process of claim 1, wherein the tail gas at a temperature of 40-60° C., a pressure of 2.6-2.8 MPa, and a flow rate of 2000 m$^3$/hr-6000 m$^3$/hr is charged into a gas washing column, and contacts with top-down desalted water reversely in the column, and the acetic acid content in the acetic acid tail gas at the outlet of the gas washing column is equal to or less than 100 ppm; wherein the tail gas from the gas washing column is charged into a mist eliminator to further remove droplets entrained therein, and the liquid level of the mist eliminator is controlled at 150-200 mm; wherein the tail gas from the mist eliminator is charged into a combined filter with a filter accuracy is 0.01 μm; and wherein the tail gas from the combined filter is heated to 40-60° C. by a heater.

11. The process of claim 10, wherein the tail gas is charged into a Prism membrane separator at a pressure increasing rate equal to or less than 0.3 MPa/min.

12. The process of claim 11, wherein after membrane separation the tail gas is charged into a compressor at a flow rate of 1000 m$^3$/h-3000 m$^3$/h.

13. The process of claim 12, wherein the circulation of the desalted water of the gas washing column is from 0.5 to 1.0 m$^3$/h.

14. The process of claim 1, wherein the acetic acid is hydrogenated with the separated hydrogen and fresh hydrogen.

15. The process of claim 1, wherein the methanol is derived from a carbon source selected from the group consisting of natural gas, oil, petroleum, coal, biomass, and combinations thereof.

16. The process of claim 1, wherein the hydrogenation catalyst comprises platinum or palladium.

17. A process for forming ethanol from methanol, comprising carbonylating the methanol to form acetic acid, and hydrogenating the acetic acid to form ethanol, wherein at least some hydrogen for the hydrogenating step is derived from a tail gas stream formed in the carbonylation step.

18. The process of claim 17, wherein the tail gas stream comprises at least 18 vol. % hydrogen.

19. The process of claim 17, wherein the tail gas stream comprises at least 25 vol. % hydrogen.

20. The process of claim 17, further comprising separating the tail gas to form a hydrogen stream and a carbon monoxide stream.

21. The process of claim 20, further comprising recycling at least a portion of the carbon monoxide stream to the carbonylation reactor.

22. The process of claim 20, further comprising methanating at least a portion of the hydrogen stream to remove residual carbon monoxide.

23. The process of claim 22, wherein the methanated stream comprises at least 85 vol. % hydrogen.

24. The process of claim 22, wherein the methanated stream comprises less than 2 vol. % carbon monoxide.

25. The process of claim 22, further comprising directing at least a portion of the methanated stream to the hydrogenation unit.

26. The process of claim 20, further comprising directing the hydrogen stream to a secondary carbonylation unit and carbonylating methanol therein with residual carbon monoxide contained in the hydrogen stream to form a secondary carbonylated stream comprising acetic acid and hydrogen.

27. The process of claim 26, wherein the secondary carbonylated stream comprises less than 2 vol. % carbon monoxide.

28. The process of claim 26, further comprising directing at least a portion of the secondary carbonylated stream to the hydrogenation unit.

29. The process of claim 17, wherein the methanol is derived from a carbon source selected from the group consisting of natural gas, oil, petroleum, coal, biomass, and combinations thereof.

30. The process of claim 17, wherein the hydrogenating occurs in the presence of a catalyst comprising platinum or palladium.

* * * * *